United States Patent
Zheng et al.

(10) Patent No.: US 10,711,291 B2
(45) Date of Patent: Jul. 14, 2020

(54) RECOMBINANT ENGINEERED BACTERIUM CO-EXPRESSING TRANS-ANETHOLE OXYGENASE AND FORMATE DEHYDROGENASE AND APPLICATION THEREOF IN PRODUCTION OF PIPERONAL

(71) Applicant: Jiangnan University, Wuxi (CN)

(72) Inventors: Pu Zheng, Wuxi (CN); Dan Wu, Wuxi (CN); Peng Wen, Wuxi (CN); Pengcheng Chen, Wuxi (CN); Yin Fu, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 0 days.

(21) Appl. No.: 16/517,792

(22) Filed: Jul. 22, 2019

(65) Prior Publication Data

US 2020/0010864 A1  Jan. 9, 2020

Related U.S. Application Data

(63) Continuation of application No. PCT/CN2018/094507, filed on Jul. 4, 2018.

(30) Foreign Application Priority Data

Apr. 22, 2019 (CN) .......................... 2019 1 03219780

(51) Int. Cl.
C12P 17/04 (2006.01)
C12N 9/04 (2006.01)
C12N 9/02 (2006.01)

(52) U.S. Cl.
CPC ............ *C12P 17/04* (2013.01); *C12N 9/0006* (2013.01); *C12N 9/0077* (2013.01); *C12Y 101/99033* (2013.01)

(58) Field of Classification Search
CPC ..... C12P 17/04; C12N 9/0077; C12N 9/0006; C12Y 101/99033
See application file for complete search history.

(56) References Cited

PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Han et al., Applied and Environmental Microbiology 78(15):5238-5246, 2012.*
Berrios-Rivera et al., Metabolic Engineering 4:217-229, 2002.*
Han et al., Journal of Agricultural and Food Chemistry 60:11972-11979, 2012.*
Li et al., International Journal of Obesity 38:140-147, 2014.*

* cited by examiner

*Primary Examiner* — Delia M Ramirez
(74) *Attorney, Agent, or Firm* — IPro, PLLC

(57) ABSTRACT

The present application discloses a method for producing piperonal by using a recombinant engineered bacterium co-expressing trans-anethole oxygenase and formate dehydrogenase, and an engineered bacterium thereof, including constructing a formate dehydrogenase gene fdh and trans-anethole oxygenase gene tao or trans-anethole oxygenase mutant gene co-expression recombinant vector; inductively expressing recombinant genetically engineered bacterium; and producing piperonal by using the recombinant genetically engineered bacterium. 15.91 g/L of piperonal with a transformation rate of 79.55% and a time-space transformation rate of 2.27 g/L/h can be finally obtained during catalysis, and the yield is significantly improved compared with the existing piperonal, thereby being more conducive to the smooth realization of industrial production.

11 Claims, 1 Drawing Sheet
Specification includes a Sequence Listing.

SEQUENCE LISTING

```
<160> NUMBER OF SEQ ID NOS: 7

<210> SEQ ID NO 1
<211> LENGTH: 1095
<212> TYPE: DNA
<213> ORGANISM: Artificial Sequence
<220> FEATURE:
<223> OTHER INFORMATION: Synthetic DNA

<400> SEQUENCE: 1
atgaaaattg tgctggtgct gtatgatgcc ggcaaacatg ccgccgatga agagaagctg      60
tacggttgca ccgagaacaa actgggcatt gccaactggc tgaaagatca aggtcacgag     120
ctgattacca caagcgataa agagggcggc aacagcgttc tggatcagca catcccggac     180
gccgatatca ttatcaccac cccgttccat ccggcctata ttaccaaaga gcgcatcgat     240
aaagccaaaa agctgaaact ggtggtggtg gccggcgtgg gtagcgatca tattgattta     300
gactatatta accagaccgg caagaagatc agcgtgctga agttaccgg cagcaacgtg      360 gtgagcgttg cagagcatgt ggtgatgacc atgctggtgt tagtgcgcaa cttcgtgccg     420
gcacacgagc agattatcaa ccacgactgg gaagtggccg ccattgccaa agacgcctac     480
gacattgagg gcaagacaat tgccaccatc ggtgccggtc gcattggtta tcgcgtgctg     540
gagcgtttag tgccgttcaa cccgaaggag ctgctgtact acgactatca agctttaccg     600
aaagatgccg aagaaaaagt gggcgcccgc cgcgtggaaa atattgagga actggtggcc     660
caagctgaca tcgtgaccgt gaacgccccg ttacacgccg caccaaagg tctgatcaat     720 aaagaactgt taagcaagtt caaaaagggc gcttggctgg ttaataccgc acgcggtgcc     780
atttgtgtgg cagaagatgt tgcagcagct ttagaaagcg gtcaactgcg cggctatggc     840
ggcgatgtgt ggtttccgca gcccgctccg aaagatcacc cgtggcgcga catgcgtaac     900
aaatatggcg ccggcaatgc catgacccct cactattctg gtaccacact ggatgcccag     960
acccgctatg cacaaggtac caaaaacatt ctggaaagct ttttcaccgg caagtttgac    1020
tatcgcccgc aagatatcat tttactgaac ggcgaatatg ttaccaaagc ctatggcaaa    1080
catgataaga aataa                                                     1095

<210> SEQ ID NO 2
<211> LENGTH: 1047
<212> TYPE: DNA
<213> ORGANISM: Pseudomonas putida

<400> SEQUENCE: 2
atggaggaca tcatgcaagg caccaacgca gcggttagcg acaaccgcgg atacaaatgg      60
atagccaggg aaatagagcg gctggaccct gaaaaggact tgccgaaat ctggcggctg     120 tccacaacgt actatgtgaa cgactttgtg atgaacctgg tttacacgct gggcatccct     180
gcttttaccc aaccgccggc gggcagcgtc gtgatgggag taacgacaga aaaagccatc     240
aaaaaaccgc agaagcgtac cgacgacacc ttgcagcatt tttggacctg gttcgaatac     300
```

```
gggccggatg atccgaggat gcaagcttca ttggcgcatg tgaatcgcgg gcatgcagca    360
cttgccaagc gttccctgg tacattcccg gctcgcgatg tgatctatac cacagcctgg    420
atcggggcca acctgcaccg cttgcgcctg agcgtcggtc ttccgggttt taccaaaaat    480
cagcaaatcg cttcgcagcg ctactgggcc gctatctgcc ggcaattctg gagtgaagac    540
ggtttagtca ctgagtatcc ggaaagcttc gaggccatgc tgcagtacat cgaggattac    600
gaagcccagc catgggaaca ggttgaatcc gggcgagtgc tgaccgaggc catcatcaag    660
caattcgtgg atgcctactt cccaggccca ttagggtgga ttggccgtca actctatctc    720
tcgttccagc ttcccaccat caacggcttg atgcagtccg ggaaacctaa cccgatcatg    780
aagtgggtga tgcgaaaggg cctgtggttc ggcttaacgc ttcaggagcg tgtcttcccc    840
gacccgaaat tatcaactcc agaaaaggcg cgcaggaaac cggtacgccc aggccaacac    900
attgatccgc ctacagccga ggtgaaatgt cctttccctg gagcgactag ccaaccctcc    960
ataccgtccg ccgattcatc tggttgccct ttccacgctg gcaaagcgaa cggggaagcc    1020
aacaattccg acttgaggac taactga                                       1047

<210> SEQ ID NO 3
<211> LENGTH: 1047
<212> TYPE: DNA
<213> ORGANISM: Artificial Sequence
<220> FEATURE:
<223> OTHER INFORMATION: Synthetic DNA

<400> SEQUENCE: 3
atggaggaca tcatgcaagg caccaacgca gcggttagcg acaaccgcgg atacaaatgg     60
atagccaggg aaatagagcg gctggaccct gaaaaggact ttgccgaaat ctggcggctg    120
tccacaacgt actatgtgaa cgactttgtg atgaacctgg tttacacgct gggcatccct    180
gcttttaccc aaccgccggc gggcagcgtc ttgatgggag taacgacaga aaaagccatc    240
aaaaaaccgc agaagcgtac cgacgacacc ttgcagcatt tttggacctg gttcgaatac    300
gggccggatg atccgaggat gcaagcttcg ttggcgcatg tgaatcgcgg gcatgcagca    360
cttgccaagc gttccctgg tacattcccg gctcgcgatg tgatctatac cacagcctgg    420
atcggggcca acctgcaccg cttgcgcctg agcgtcggtc ttccgggttt taccaaaaat    480
cagcaaatcg cttcgcagcg ctactgggcc gctatctgcc ggcaattctg gagtgaagac    540
ggtttagtca ctgagtatcc ggaaagcttc gaggccatgc tgcagtacat cgaggattac    600
gaagcccagc catgggaaca ggttgaatcc gggcgagtgc tgaccgaggc catcatcaag    660
caattcgtgg atgcctactt cccaggccca ttagggtgga ttggccgtca actctatctc    720
tcgttccagc ttcccaccat caactgcttg atgcagtccg ggaaacctaa cccgatcatg    780
aagtgggtga tgcgaaaggg cctgtggttc ggcttaacgc ttcaggagcg tgtcttcccc    840
gacccgaaat tatcaactcc agaaaaggcg cgcaggaaac cggtacgccc aggccaacac    900
attgatccgc ctacagccga ggtgaaatgt cctttccctg gagcgactag ccaaccctcc    960
ataccgtccg ccgattcatc tggttgccct ttccacgctg gcaaagcgaa cggggaagcc    1020
aacaattccg acttgaggac taactga                                       1047

<210> SEQ ID NO 4
<211> LENGTH: 44
<212> TYPE: DNA
<213> ORGANISM: Artificial Sequence
<220> FEATURE:
<223> OTHER INFORMATION: Synthetic DNA
```

```
<400> SEQUENCE: 4
ccacagccag gatccgaatt catgaaaatt gtgctggtgc tgta                    44

<210> SEQ ID NO 5
<211> LENGTH: 50
<212> TYPE: DNA
<213> ORGANISM: Artificial Sequence
<220> FEATURE:
<223> OTHER INFORMATION: Synthetic DNA

<400> SEQUENCE: 5
cgacttaagc attatgcggc cgcttatttc ttatcatgtt tgccataggc              50

<210> SEQ ID NO 6
<211> LENGTH: 42
<212> TYPE: DNA
<213> ORGANISM: Artificial Sequence
<220> FEATURE:
<223> OTHER INFORMATION: Synthetic DNA

<400> SEQUENCE: 6
agatatacat atggcagatc tatggaggac atcatgcaag gc                      42

<210> SEQ ID NO 7
<211> LENGTH: 46
<212> TYPE: DNA
<213> ORGANISM: Artificial Sequence
<220> FEATURE:
<223> OTHER INFORMATION: Synthetic DNA

<400> SEQUENCE: 7
ggtttcttta ccagactcga gtcagttagt cctcaagtcg gaattg                  46
```

RECOMBINANT ENGINEERED BACTERIUM CO-EXPRESSING TRANS-ANETHOLE OXYGENASE AND FORMATE DEHYDROGENASE AND APPLICATION THEREOF IN PRODUCTION OF PIPERONAL

TECHNICAL FIELD

The disclosure herein relates to the field of biocatalysis, and particularly relates to a method for producing piperonal by using a recombinant engineered bacterium co-expressing trans-anethole oxygenase and formate dehydrogenase and an engineered bacterium thereof.

BACKGROUND

Piperonal, also known as heliotropin, has a sweet cherry and vanilla aroma. The piperonal is widely applied in food flavor, cosmetic, pharmaceutical, agricultural and electroplating industries. Natural heliotropinis mainly found in plants such as melon, *Robinia pseudoacacia*, allspice, and vanilla beans, but the content is extremely small, and people cannot directly extract the natural heliotropin from plants.

At present, the heliotropin is industrially produced mainly by a semi-synthesis method using safrole as a raw material and a total synthesis method using catechol as a raw material. The method seriously pollutes the environment and consumes much energy. With the increasing attention of people on the material production process and the increasing requirements for food additives, flavor substances synthesized by a bio-fermentation method and enzymatic method are increasingly favored by people.

Microbial synthesis of piperonal is currently not applied to industrial production. The Santos team in Brazil found several strains of microbes of producing piperonal with isosafrole. The most efficient strain is *Paecilomyces variot bainier*, but only under the condition that $H_2O_2$ is added, the highest yield is 64 mg/L, and the transformation rate is only 20%. In Chinese patent CN105779363A, it is found that a strain of *Serratia liquefaciens* produces 282 mg/L of piperonal.

Therefore, how to improve enzyme activity of trans-anethole oxygenase and accelerate catalytic synthesis rate of piperonal is a technical problem to be solved urgently in the field of microbial synthesis of piperonal.

SUMMARY

The present disclosire provides a recombinant engineered bacterium co-expressing trans-anethole oxygenase and formate dehydrogenase used for producing piperonal, wherein a gene fdh encoding the formate dehydrogenase, and a gene tao encoding the trans-anethole oxygenase or a gene $tao_{3g2}$ encoding a trans-anethole oxygenase mutant are connected in series to a pETDuet-1 vector. Preferably, the gene fdh encoding the formate dehydrogenase is located at a first multiple cloning site MSC1 of the pETDuet-1 vector, and the gene tao encoding the trans-anethole oxygenase or the gene $tao_{3g2}$ encoding the trans-anethole oxygenase mutant is located at a second multiple cloning site MSC2 of the pETDuet-1 vector.

In an embodiment of the present application, a nucleotide sequence of the trans-anethole oxygenase gene tao is shown in SEQ ID NO.2; a nucleotide sequence of the trans-anethole oxygenase mutant gene $tao_{3g2}$ is shown in SEQ. ID NO.3; the formate dehydrogenase gene fdh is derived from *Candida boidinii*, and a nucleotide sequence thereof is shown in SEQ ID NO.1 after codon optimization.

In an embodiment of the present application, the recombinant engineered bacterium uses *E. coli* BL21(DE3) as a host.

The present application also provides a method for producing piperonal by using the recombinant engineered bacterium co-expressing Trans-Anethole Oxygenase and formate dehydrogenase. The method comprises the following steps:

(1) preparing a biocatalyst,
(2) by using safrole as a substrate and sodium formate as a cosubstrate, catalytically synthesizing piperonal with the biocatalyst.

In an embodiment of the present application, in step (1), the formate dehydrogenase gene fdh and the trans-anethole oxygenase gene tao or the trans-anethole oxygenase mutant gene $tao_{3g2}$ co-expression recombinant vector transform the *E. coli* BL21(DE3) strain, then are inoculated in an LB medium containing 30 to 100 mg/L ampicillin, and cultured to obtain a seed solution; and then the seed solution is inoculated in the LB medium containing 30 mg/L to 100 mg/L ampicillin in an amount of 2% to 5% and cultured at a temperature of 37° C. until $OD_{600\,nm}$ is 0.5 to 1.8, and IPTG with a final concentration of 0.1 mmol/L to 1 mmol/L is added, inductively cultured at a temperature of 16° C. to 28° C. for 6 h to 10 h, and centrifuged to collect thallus cells.

In an embodiment of the present application, in step (2), a reaction system is constituted by using the safrole as the substrate, the sodium formate as the cosubstrate, and a buffer with pH of 3 to 9 as a reaction medium, the transformation is carried out at a temperature of 20° C. to 40° C. and a speed of 50 rpm~240 rpm for 0.5 h to 12 h.

In an embodiment of the present application, in step (2), the substrate concentration is 1 g/L to 30 g/L, the cosubstrate concentration is 1 g/L to 60 g/L, and the amount of the biocatalyst is 10 to 100 g/L calculated by a wet weight of a thallus.

The present application has the beneficial effects that are combinant genetically engineered bacterium is obtained by constructing the recombinant vectors co-expressing the formate dehydrogenase gene and the trans-anethole oxygenase gene or the trans-anethole oxygenase mutant gene, 15.91 g/L piperonal with a transformation rate of 79.55% and a time-space transformation rate of 2.27 g/L/h is finally obtained during catalysis, and the yield is significantly improved compared with the existing piperonal, thereby being more conducive to the smooth realization of industrial production.

DETAILED DESCRIPTION

Example 1

Cloning of formate dehydrogenase gene fdh and trans-anethole oxygenase gene tao (and mutant gene thereof) and construction of a co-expression recombinant system:

A nucleotide sequence of the gene fdh encoding the formate dehydrogenase was shown in SEQ ID NO.1, which was derived from *Candida boidinii* (GenBank: AJ011046.2)

and codon-optimized, and the codon-optimized nucleotide sequence was shown in SEQ ID NO.1. The codon-optimized gene fdh encoding the formate dehydrogenase was connected to a vector pET-28a to obtain a recombinant vector pET-28a-fdh; a nucleotide sequence of the gene tao encoding the trans-anethole oxygenase was shown in SEQ ID NO.2, which was derived from *Pseudomonas putida*, and a nucleotide sequence of the trans-anethole oxygenase mutant gene $tao_{3g2}$ is shown in SEQ ID NO.3. The trans-anethole oxygenase activity of the mutant encoded by the gene$tao_{3g2}$ was improved by about 1.4 times compared with the activity of the enzyme encoded by the gene tao.

Figure 1:
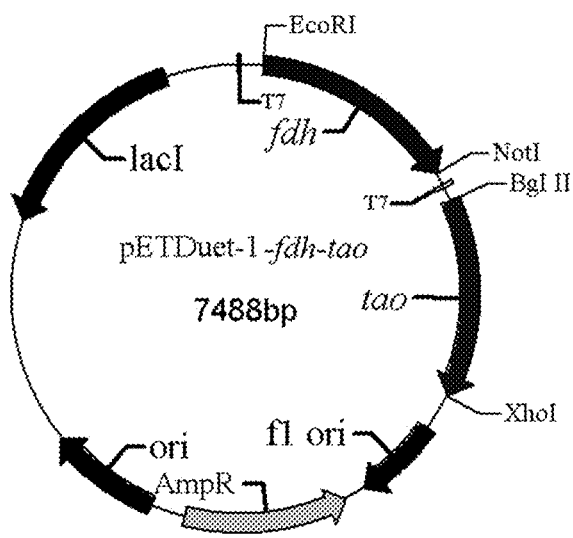
FIG. 1 is a vector map of a trans-anethole oxygenase and formate dehydrogenase co-expression vectorpETDuet-1-fdh-tao in the present application.

(1) Construction of Co-Expression Recombinant Vectors pETDuet-1-Fdh-Too and pETDuet-1-Fdh-Tao$_{3g2}$:

PCR amplification (using PrimeSTAR® Max DNA Polymerase, TaKaRa) was carried out by using pET-28a-fdh as a template through upstream and downstream primers (upstream: 5'-ccacagccaggatccgaattcatgaaaattgtgctggtgctgta-3', see SEQ ID NO.4; downstream: 5'-cgacttaagcattatgc ggccgcttatttcttatcatgtttgccataggc-3', see SEQ ID NO.5) to obtain a product containing the formate dehydrogenase gene. A plasmid pETDuet-1 (MSC1) was double-digested with EcoRI and NotI, and a linear plasmid was recovered, and then a recombinant plasmid pETDuet-1-fdh was obtained by onestep cloning. Subsequently, by designing upstream and downstream primers (upstream: 5'-agatata catatggcagatctatggaggacatcatgcaaggc-3', see SEQ ID NO.6; downstream: 5'-ggtttctttaccagac tcgagtcagttagtcctcaagtcggaattg-3', SEQ ID NO.7) to carry out the PCR amplification to obtain the trans-anethole oxygenase gene tao (and a mutant gene tao$_{3g2}$ thereof). A plasmid pETDuet-1-fdh (MSC2) was first double-digested with BglII and XhoI, and a linear plasmid was recovered, and then a recombinant plasmid pETDuet-1-fdh-tao was obtained by one step cloning. By using the same method, a co-expression recombinant vector pETDuet-1-fdh-tao$_{3g2}$ of the formate dehydrogenase and the trans-anethole oxygenase mutant was obtained by construction (as shown in FIG. 1). In the above process, the PCR reaction conditions were: 94° C. for 5 min; 98° C. for 10 s, 56° C. for 5 s, 72° C. for 15 s (35 cycles); and 72° C. for 10 min. After the end of PCR, a target gene fragment was recovered by using a PCR product purification kit (PCR product purification kit, GENERay Company). The specific method of onestep cloning (using One Step Cloning Kit, Vazyme Company) includes steps of mixing the target gene fragment (0.04 to 0.08 ng/bp) with the vector (0.005 to 0.01 ng/bp) in the same PCR tube, adding 2 to 4 μL of a recombinase buffer (5×CEllBuffer) and 1 to 2 μL of recombinase (Exnase II), adding ddH$_2$O to supplement to 10 to 20 μL, and reacting at a temperature of 37° C. for 30 min to obtain a recombinant plasmid. PETDuet-1-tao-fdhis obtained by exchanging locations of multiple cloning sites of the above formate dehydrogenase and trans-anethole oxygenase.

(2) Construction of Double Plasmids Expression Vector:

In consideration of the fact that the trans-anethole oxygenase plays a major role in the catalytic synthesis reaction of piperonal, the formate dehydrogenase was cloned into a plasmid pCDFDuet-1 with a lower copy number to finally obtain pCDFDuet-1-fdh. The gene tao was connected to pETDuet-1 to obtain pETDuet-1-tao. PCDFDuet-1-fdh constitutes a double plasmid expression vector with pETDuet-1-tao and pETDuet-1-fdh-tao, respectively.

(3) Construction of Co-Expression Recombinant Vector pETDuet-1-Tao-Fdh:

On the basis of pETDuet-1-fdh-tao, the order of fdh and tao was adjusted to obtain pETDuet-1-tao-fdh.

On the basis of pETDuet-1-fdh-tao$_{3g2}$, the order of fdh and tao was adjusted to obtain pETDuet-1-tao$_{3g2}$-fdh.

(4) Construction of Other Expression Vectors

Referring to Tables 3 to 5, tao (or tao$_{3g2}$) and fdh were cloned into pCDFDuet-1, pACYCDuet-1, pRSFDuet-1, and pCOLADuet-1 plasmids by using a method similar to the above (1) to obtain different co-expression systems.

The vectors constructed in the above (1) to (4) were separately transferred into *E. coli* BL21(DE3), and screened to obtain positive transformants, namely, co-expression strains.

Example 2

Inducible expression of recombinant genetically engineered bacteria of different co-expression systems:

Different co-expression strains obtained in the above Example 1 were inoculated respectively in an LB medium containing 30 to 100 mg/L ampicillin, and cultured at a temperature of 37° C. overnight to obtain a seed solution; then the seed solution was inoculated in the LB medium containing 30 to 100 mg/L ampicillin in an amount of 2 to 5% until OD$_{600\ nm}$ was 0.5 to 1.8, and was added with IPTG with a final concentration of 0.1 to 1 mmol/L and inductively cultured at a temperature of 16 to 28° C. for 6 to 10 h. Finally, the culture was centrifuged at a temperature of 4° C. and a speed of 5,000-8,000 rpm for 8 to 15 min, and a supernatant was discarded to obtain the cells, and the cells were washed twice with normal saline, and centrifuged to collect cells, namely, a biocatalyst.

Example 3

Comparison of trans-anethole oxygenase activity of different co-expression strains:

The determination method of trans-anethole oxygenase (TAO) activity includes the following steps: adding an appropriate amount of biocatalyst as well as safrole and sodium formate in a reaction system, reacting at a temperature of 30° C. for 20 min, taking a certain volume of reaction solution, adding an equal volume of methanol and uniformly mixing, terminating the reaction, centrifuging at a speed of 10,000 rpm for 5 min, filtering a supernatant through a 0.22 μm membrane, and detecting the content of piperonal by HPLC. The trans-anethole oxygenase activity (U) was defined as the amount of enzyme required to produce 1 μmol/L piperonal per minute when the thallus OD$_{600\ nm}$ is equal to 1.

The determination method of formate dehydrogenase activity (FDH) includes the following steps: carrying out the determination method at a temperature of 30° C. for consecutive 10 min, measuring OD$_{340\ nm}$ at an interval of 1 min, placing 200 μL of a reaction buffer containing 10 mmol/L sodium phosphate buffer (pH=7.5), 167 mmol/L sodium formate, and 1.67 mmol/L NAD$^+$ in ELIASA and preheating for 10 min, and adding 100 μL of a crude enzyme solution to start the reaction. The formate dehydrogenase activity (U) was defined as the amount of enzyme required to produce 1 μmol of NADH per minute.

The determination method of piperonal content was an HPLC method. HPLC detection conditions were as follows: an Amethst C18-H reverse column (4.6 mm×250 mm, 5 μm) was adopted, 60% acetonitrile, and 0.1% formic acid were used as a mobile phase, the column oven temperature was 35° C., the injection volume was 10 μL, and the piperonal content was detected at 270 nm.

The strains for comparing the enzyme activity were as follows: E. coli BL21(DE3)pETDuet-1-tao, E. coli BL21 (DE3)pETDuet-1-fdh-tao, E. coli BL21(DE3)pETDuet-1-tao-fdh, E. coli BL21(DE3)pETDuet-1-tao$_{3g2}$-fdh, E. coli BL21(DE3)pETDuet-1-tao/pCDFDuet-1-fdh, E. coli BL21 (DE3)pETDuet-1-fdh-tao/pCDFDuet-1-fdh, etc. (Tables 1 to 5).

By comparing the TAO enzyme activity with the FDH enzyme activity, it was found that the trans-anethole oxygenase activity and the formate dehydrogenase activity were shown at different levels in co-expression systems constructed based on different plasmids (pETDuet-1, pCDFDuet-1, pACYCDuet-1, pRSFDuet-1, and pCOLADuet-1). Compared with other plasmids, pETDuet-1 was selected as a plasmid to co-express FDH and TAO, and better results were obtained. PETDuet-1 was selected as a plasmid to co-express FDH and TAO mutants to obtain a recombinant genetically engineered strain E. coli BL21(DE3)pETDuet-1-fdh-tao$_{3g2}$. The enzyme activity of the trans-anethole oxygenase mutant was 205U.

TABLE 1

Comparison of trans-anetholee monooxygenase activity and formate dehydrogenase activity of different co-expression strains constructed by mainly using pETDuet-1 plasmid

| Co-expression strains | TAO(U) | FDH(U) |
|---|---|---|
| E. coli BL21(DE3)pETDuet-1-tao | 38.48 | — |
| E. coli BL21(DE3)pET-28a-fdh | — | 67.39 |
| E. coli BL21(DE3)pET-28a-fdh-tao | 20.21 | 11.73 |
| E. coli BL21(DE3)pET-28a-tao-fdh | 32.42 | 2.83 |
| E. coli BL21(DE3)pETDuet-1-tao-fdh | 62.34 | 5.74 |
| E. coli BL21(DE3)pETDuet-1-fdh-tao | 182.82 | 26.03 |
| E. coli BL21(DE3)pETDuet-1-tao&pCDFDuet-1-fdh | 66.79 | 14.98 |
| E. coli BL21(DE3)pETDuet-1-fdh-tao&pCDFDuet-1-fdh | 168.51 | 27.66 |
| E. coli BL21(DE3)pETDuet-1-fdh-tao$_{3g2}$ | 205.26 | 27.20 |

Note:
"—" means that no activity was detected.

TABLE 2

Comparison of trans-anetholee monooxygenase activity and formate dehydrogenase activity of different co-expression strains constructed by mainly using pCDFDuet-1 plasmid

| Co-expression strains | TAO(U) | FDH(U) |
|---|---|---|
| E. coli BL21 (DE3) pCDFDuet-1-tao | 20.74 | — |
| E. coli BL21 (DE3) pCDFDuet-1-tao-fdh | 33.96 | 4.22 |
| E. coli BL21 (DE3) pCDFDuet-1-fdh-tao | 91.05 | 18.43 |
| E. coli BL21 (DE3) pCDFDuet-1-tao&pETDuet-1-fdh | 53.28 | 19.57 |
| E. coli BL21 (DE3) pCDFDuet-1-fdh-tao&pETDuet-1-fdh | 101.71 | 24.58 |
| E. coli BL21 (DE3) pCDFDuet-1-fdh-tao$_{3g2}$&pETDuet-1-fdh | 115.73 | 22.59 |

Note:
"—" means that no vitality was detected.

TABLE 3

Comparison of trans-anethole oxygenase activity and formate dehydrogenase activity of different co-expression strains constructed by mainly using pACYCDuet-1 plasmid

| Co-expression strains | TAO(U) | FDH(U) |
|---|---|---|
| E. coli BL21 (DE3) pACYDuet-1-tao | 9.07 | — |
| E. coli BL21 (DE3) pACYDuet-1-tao-fdh | 12.54 | 2.68 |

TABLE 3-continued

Comparison of trans-anethole oxygenase activity and formate dehydrogenase activity of different co-expression strains constructed by mainly using pACYCDuet-1 plasmid

| Co-expression strains | TAO(U) | FDH(U) |
|---|---|---|
| E. coli BL21 (DE3) pACYDuet-1-fdh-tao | 30.89 | 9.36 |
| E. coli BL21 (DE3) pACYDuet-1-tao&pETDuet-1-fdh | 10.36 | 20.64 |
| E. coli BL21 (DE3) pACYDuet-1-fdh-tao&pETDuet-1-fdh | 5.38 | 23.82 |
| E. coli BL21 (DE3) pACYDuet-1-fdh-tao$_{3g2}$ | 42.37 | 7.01 |

Note:
"—" means that no activity was detected.

TABLE 4

Comparison of trans-anethole oxygenase activity and formate dehydrogenase activity of different co-expression strains constructed by mainly using pRSFDuet-1 plasmid

| Co-expression strains | TAO(U) | FDH(U) |
|---|---|---|
| E. coli BL21(DE3)pRSFDuet-1-tao | 19.77 | — |
| E. coli BL21(DE3)pRSFDuet-1-tao-fdh | 33.69 | 2.71 |
| E. coli BL21(DE3)pRSFDuet-1-fdh-tao | 127.03 | 20.82 |
| E. coli BL21(DE3)pRSFDuet-1-tao&pETDuet-1-fdh | 60.42 | 26.79 |
| E. coli BL21(DE3)pRSFDuet-1-fdh-tao&pETDuet-1-fdh | 93.45 | 28.00 |
| E. coli BL21(DE3)pRSFDuet-1-fdh-tao$_{3g2}$ | 162.44 | 16.93 |

Note:
"—" means that no activity was detected.

TABLE 5

Comparison of trans-anethole oxygenase activity and formate dehydrogenase activity of different co-expression strains constructed by mainly using pCOLADuet-1 plasmid

| Co-expression strains | TAO(U) | FDH(U) |
|---|---|---|
| E. coli BL21(DE3)pCOLADuet-1-tao | 17.58 | — |
| E. coli BL21(DE3)pCOLADuet-1-tao-fdh | 29.35 | 2.03 |
| E. coli BL21(DE3)pCOLADuet-1-fdh-tao | 100.63 | 18.26 |
| E. coli BL21(DE3)pCOLADuet-1-tao&pETDuet-1-fdh | 58.27 | 23.47 |
| E. coli BL21(DE3)pCOLADuet-1-fdh-tao&pETDuet-1-fdh | 101.93 | 31.84 |
| E. coli BL21(DE3)pCOLADuet-1-fdh-tao$_{3g2}$&pETDuet-1-fdh | 112.30 | 29.04 |

Example 4

Figure 2:
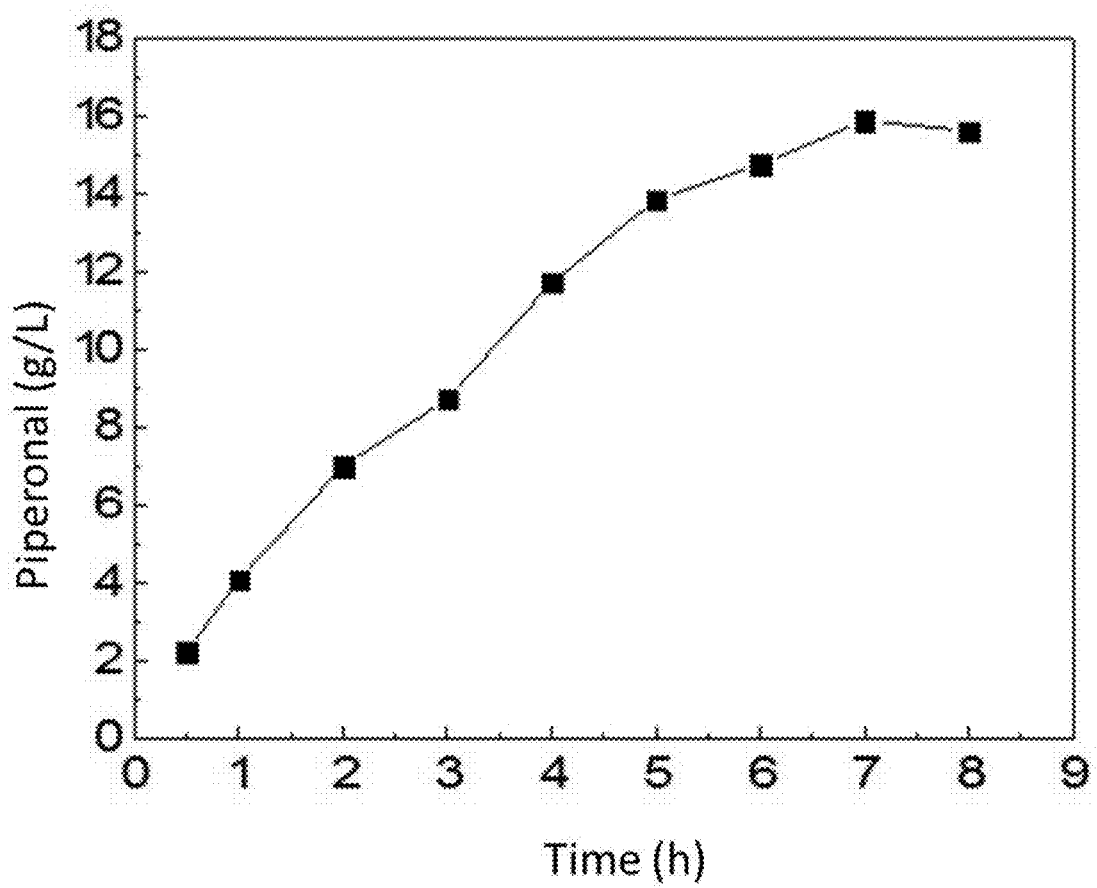
FIG. 2 is production of piperonal by *E. coli* BL21(DE3) pETDuet-1-fdh-$tao_{3g2}$ using safrole as a substrate.

Production of piperonal by E. coli BL21(DE3)pETDuet-1-fdh-tao$_{3g2}$ using safrole as a substrate:

The strain E. coli BL21(DE3)pETDuet-1-fdh-tao$_{3g2}$ with the highest trans-anethole oxygenase activity obtained in Example 3 was inductively expressed according to the method in Example 2 to prepare a biocatalyst. In a PBS buffer with pH of 7.4, 7.5% of biocatalyst, 20 g/L safrole and 40 g/L sodium formate were added, the transformation was carried out at a temperature of 30° C. and a speed of 110 rpm for 8 h, and the product generation situation was observed by sampling every 1 h. As shown in FIG. 2, when the transformation was carried out by using the 20 g/L substrate, the piperonal with a yield of 15.91 g/L, a transformation rate of 79.55%, and a space-time transformation rate of 2.27 g/L/h was finally obtained.

In summary, the recombinant genetically engineered bacterium is obtained by constructing the recombinant vector co-expressing the formate dehydrogenase gene and the trans-anethole oxygenase gene (and the mutant gene thereof) according to the present application. The mechanism is as follows: during the catalytic reaction, the concentration of FADH in the catalytic reaction is improved by providing NADH to reduce the prosthetic group FAD of TAO. The experimental results show that the method provided by the present application greatly improves the overall catalytic efficiency, 15.91 g/L piperonal with the transformation rate of 79.55% and the time-space transformation rate of 2.27 g/L/h is finally obtained during catalysis, and the yield is significantly improved compared with the existing piperonal, thereby being more conducive to the smooth realization of industrial production.

What is claimed is:

1. A recombinant engineered bacterium for producing piperonal, which comprises:
   a gene encoding a trans-anethole oxygenase mutant having the nucleotide sequence of SEQ ID NO: 3, and a gene encoding a formate dehydrogenase that when expressed oxidizes formate;
   wherein the gene encoding the formate dehydrogenase and the gene encoding the trans-anethole oxygenase mutant are connected in series in a bacterial expression vector.

2. The recombinant engineered bacterium of claim 1, wherein the formate dehydrogenase gene is located upstream of the gene encoding the trans-anethole oxygenase mutant in the vector.

3. The recombinant engineered bacterium of claim 1, wherein the formate dehydrogenase gene is from *Candida boidinii*.

4. The recombinant engineered bacterium of claim 1, wherein the recombinant engineered bacterium is *E. coli* BL21(DE3) transformed with the vector.

5. The recombinant engineered bacterium of claim 2, wherein the formate dehydrogenase gene has the nucleotide sequence of SEQ ID NO: 1.

6. A method for producing piperonal comprising (a) culturing the recombinant engineered bacterium of claim 1, and (b) incubating safrole as a substrate and sodium formate as a cosubstrate with the recombinant engineered bacterium.

7. The method of claim 6, wherein the recombinant engineered bacterium is *E. coli* BL21(DE3) transformed with the vector.

8. The method of claim 6, wherein the formate dehydrogenase gene is from *Candida boidinii*.

9. The method of claim 6, wherein said method further comprises:
   (i) transforming an *E. coli* BL21(DE3) strain with a bacterial expression vector that comprises a gene encoding a trans-anethole oxygenase mutant having the nucleotide sequence of SEQ ID NO: 3, and a gene encoding a formate dehydrogenase that when expressed oxidizes formate, wherein the gene encoding the formate dehydrogenase and the gene encoding the trans-anethole oxygenase mutant are connected in series in the bacterial expression vector;
   (ii) incubating the transformed *E. coli* BL21(DE3) strain in a Luria broth medium comprising 30 to 100 mg/L ampicillin;
   (iii) culturing the transformed *E. coli* BL21(DE3) strain to obtain a seed solution;
   (iv) inoculating a second Luria broth medium comprising 30 to 100 mg/L ampicillin with the seed solution, wherein the inoculated second Luria broth medium comprises between 2% to 5% of seed solution;
   (v) incubating the second Luria broth medium of (iv) at a temperature of 37° C. until $OD_{600}$ is 0.5 to 1.8;
   (vi) adding isopropyl-β-D-1-thiogalactopyranoside (IPTG) to the second Luria broth medium of (v) to a final concentration of 0.1 to 1 mmol/L to induce expression from the bacterial expression vector;
   (vii) culturing the second Luria broth medium of (vi) at a temperature of 16° C. to 28° C. for 6 to 10 hours; and (viii) centrifuging the second Luria broth medium of (viii) to collect the recombinant engineered bacterium.

10. The method of claim 9, wherein safrole and sodium formate are in a buffer solution with a pH of 3 to 9, and wherein safrole and sodium formate are incubated with the recombinant engineered bacterium at a temperature of 20° C. to 40° C.

11. The method of claim 10, wherein safrole is added at a concentration of from 1 to 30 g/L, sodium formate is added at a concentration of from 1 to 60 g/L, and the recombinant engineered bacterium is present at a concentration of 10 to 100 g/L.

* * * * *